United States Patent [19]

Komarnycky

[11] 4,253,563
[45] Mar. 3, 1981

[54] MULTISTRAND SUTURE PACKAGE

[75] Inventor: Peter Komarnycky, Highbridge, N.J.

[73] Assignee: Ethicon, Inc., Somerville, N.J.

[21] Appl. No.: 150,266

[22] Filed: May 15, 1980

[51] Int. Cl.³ .............................................. A61L 15/00
[52] U.S. Cl. .................................. 206/63.3; 206/476; 206/484; 206/628
[58] Field of Search ............... 206/63.3, 438, 476–477, 206/482–484, 488, 489, 491, 492, 498; 229/85

[56] References Cited

U.S. PATENT DOCUMENTS

| 3,444,994 | 5/1969 | Kaepernik et al. | 206/63.3 |
| 3,939,696 | 2/1976 | Miller | 206/63.3 |
| 4,063,638 | 12/1977 | Marwood | 206/63.3 |
| 4,069,912 | 1/1978 | Black et al. | 206/63.3 |
| 4,089,409 | 5/1978 | Cerwin | 206/63.3 |
| 4,089,410 | 5/1978 | Bolanowski et al. | 206/63.3 |
| 4,120,395 | 10/1978 | Mandel | 206/63.3 |
| 4,126,221 | 11/1978 | Cerwin | 206/63.3 |

Primary Examiner—Joseph Man-Fu Moy
Attorney, Agent, or Firm—Wayne R. Eberhardt

[57] ABSTRACT

An improved package for a plurality of needled sutures comprising a folded suture retainer wherein a bundle of substantially aligned suture strands are coiled between two folded panels while the needles are retained between two adjacent folded panels. The needles are centered on one panel by an opening communicating with the interior of the package. A removable portion in the outer needle retaining panel provides access to the needles while the bulk of the suture remains coiled within the package.

16 Claims, 5 Drawing Figures

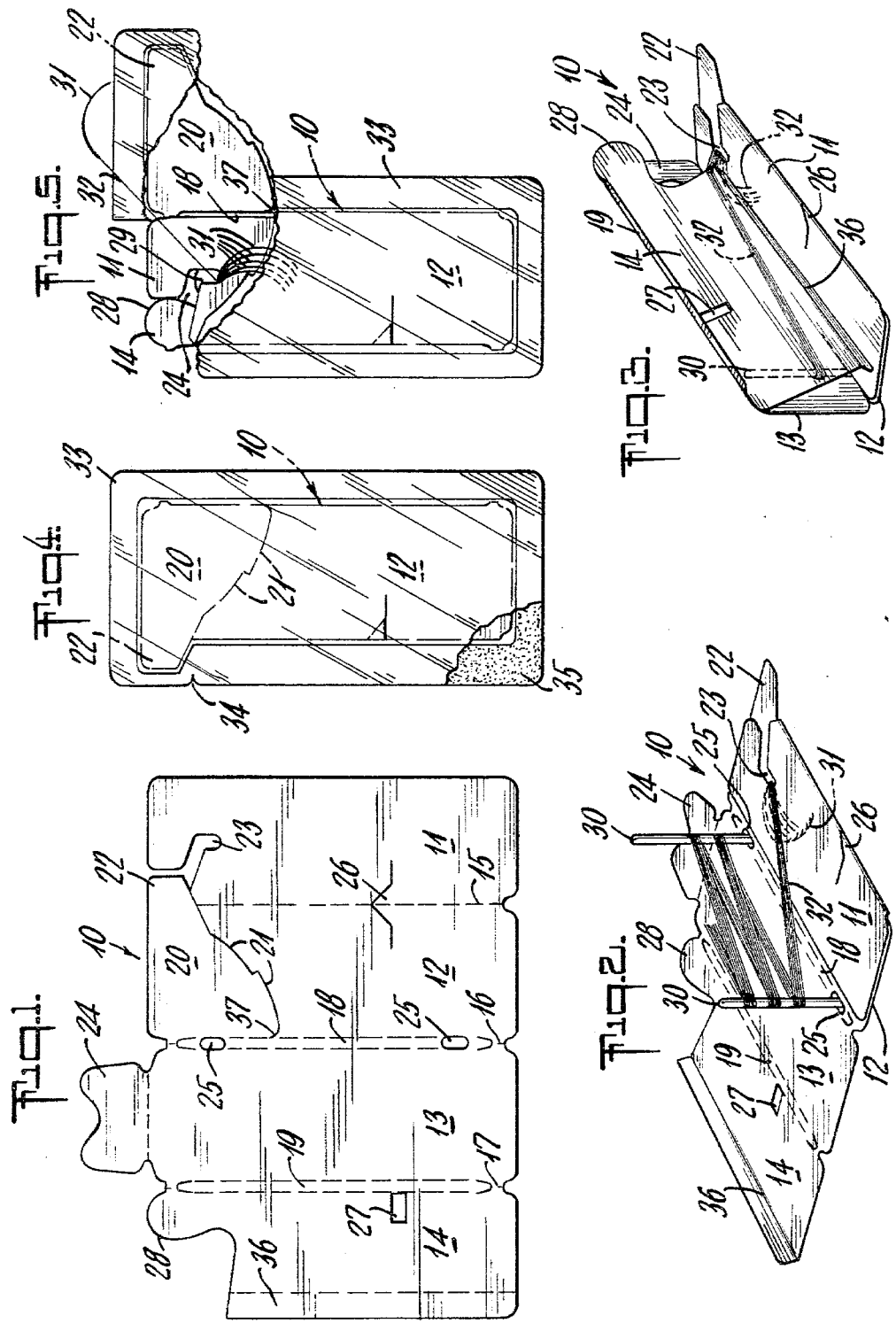

MULTISTRAND SUTURE PACKAGE

BACKGROUND OF THE INVENTION

This invention relates to packages for surgical sutures, and, more particularly, to a multipaneled, folded paper retainer for a plurality of coiled suture having needles attached thereto.

Packages for surgical sutures are constructed according to the nature of the suture and its intended use. In general, the ideal package holds and protects the suture during handling and storage yet allows the suture to be readily removed with a minimum of handling and difficulty.

A popular suture package consists of a folded paper suture retainer contained in a sterile, hermetically sealed envelope. The sterility of the suture and envelope are maintained by a second sealed outerwrap. When the suture is to be used, the outerwrap is opened in the operating room and the sealed envelope deposited in a sterile area. Sterile personnel thereupon tear open the sterile envelope to gain access to the suture.

Suture packages have recently been designed to simplify opening of the sterile envelope and improve accessibility of the suture in order to avoid unnecessary delays during surgical procedures. A major improvement in this regard is described in U.S. Pat. No. 3,939,696 where a portion of the inner suture retainer is secured to the sealed envelope so that the envelope and inner retainer may be opened simultaneously, and the end of the suture exposed for immediate pickup.

Suture packages have also been recently developed to retain a bundle of sutures in a predetermined coiled configuration which permits individual sutures to be withdrawn from the package without entangling the remaining sutures. Such multistrand packages with single strand dispensing are illustrated in U.S. Pat. Nos. 4,089,409 and 4,126,221.

The present invention represents a further improvement in packages of the multistrand type where the needled ends of the suture are automatically presented when the sterile envelope is opened. Packages of the present invention have advantages over prior art multistrand packages, particularly in regard to ease of opening and convenience of needle presentation.

It is accordingly an object of the present invention to provide an improved package for multistrand needled sutures. It is a further object of the present invention to provide an improved folded paper retainer for multistrand needled surgical sutures which permits single strand dispensing. It is an additional object of this invention to provide a suture package which allows simultaneous opening of the inner suture retainer and outer sealed envelope to provide instant access of the needled ends of the sutures. These and other objects of the invention will be apparent from the ensuing description and claims.

SUMMARY

The present invention provides an elongated, four-panel, folded suture retainer for multistrand needled sutures. The armed ends of the sutures are retained between first and second panels while the bulk of the length of the sutures is collated into a bundle of substantially aligned strands and coiled between third and fourth panels.

The desired suture configuration is conveniently obtained by winding the suture bundle about two vertical pins extending through openings in the suture retainer between the second and third panels, beginning at the bottom of the pins and winding in an upward spiral to provide a plurality of convolutions disposed in sequence over the length of the suture and laterally displaced along the length of the pins with substantially no overlap between adjacent convolutions. The sutures may be wound around the pins in a series of figure-8 or circular loops, in a series of circular loops having at least one reversal in the direction of winding, or in a combination of these. The suture package is folded to enclose the suture coils between the third and fourth panels of folder before the winding pins are removed, and the suture strands are maintained within the package as a substantially parallel bundle of filaments coiled in the form of a plurality of contiguous, overlapping convolutions with successive convolutions disposed in sequence from one end of the suture to the other and with adjacent convolutions being laterally displaced one from the other.

When the retainer is in its fully folded position, the first and fourth panels are enclosed between the second and third panels which then form the outside front and back panels of the folded retainer. The second panel is provided with a die cut diagonal, segmented tearline extending from one corner across the width of the panel which allows a portion of this panel to be removed in order to gain access to the needles retained between the first and second panels. Upon removal of this portion of the second panel, individual needles are readily grasped with a needle holder, and the suture withdrawn from between the folds of the retainer. The foldlines between the second, third and fourth panels are preferably provided with a gusset over a major portion of the length thereof. When the retainer is fully folded, these gussets create an internal chamber between the third and fourth panels to accommodate the coiled suture bundle without exerting side pressures which might interfere with individual suture removal.

The first panel is provided with a slot extending from an outside edge to a center opening in the panel. The needled ends of the sutures are passed through this slot to center the needles between the first and second panels and under the tearline of the second panel.

The folded retainer and sutures contained therein are sterilized and sealed within a conventional sterile envelope which preferably comprises aluminum foil coated with a thermoplastic polymer heat sealed around the periphery thereof. The portion of the second panel intended to be removed to gain access to the suture needles is provided with a tab extending beyond the width of the folded retainer. This tab is sealed in the border of the outer envelope so that when the envelope is opened by tearing one end, the portion of the second panel defined by the diagonal tearline is simultaneously opened to expose the needled ends of the suture.

DESCRIPTION OF DRAWINGS

FIG. 1 is a plan view of an unfolded suture retainer of the present invention.

FIG. 2 is a view in perspective of the retainer of FIG. 1 positioned over two suture winding pins with the needles of the sutures retained between the folded first and second panels and with the bulk of the suture length wound on the pins in a figure-8 pattern.

FIG. 3 is a view in perspective of the package of FIG. 2 partially folded before the package is removed from the winding pins.

FIG. 4 is a plan view of the fully folded suture retainer of FIG. 3 contained within a sealed outer envelope.

FIG. 5 is a plan view of the suture package and envelope of FIG. 4 opened to provide access to the suture needle.

DETAILED DESCRIPTION OF PREFERRED EMBODIMENT

FIGS. 1 through 5 illustrate the various stages in preparing and using an exemplary suture package of the present invention. In FIG. 1 there is illustrated an open suture retainer 10 comprising first and second needle retaining panels 11 and 12, and third and fourth suture retaining panels 13 and 14. Foldlines 15, 16, and 17 are provided between the respective panels to facilitate rapid folding and assembly of the retainer. Additionally, foldlines 16 and 17 are provided with a central gusset section 18 and 19 over a substantial portion of the length thereof, the purpose of which will be apparent from the description below.

Panel 12 is divided into two sections by segmented die cut 21 extending diagonally across the width thereof to form needle access panel 20 over the upper portion of panel 12 as illustrated. The free edge of needle access panel 20 extends beyond foldline 15 forming tab 22 which extends beyond the width of the folded retainer as hereinafter described. Die cut 21 terminates at the intersection of tab 22 with dogleg slot 23 extending into panel 11 from the upper edge thereof.

Other features of the retainer illustrated in FIG. 1 include end flap 24 extending beyond the end of panel 13 and winding pin openings 25 in gusset 18. Tab 26 formed by a die cut extending across foldline 15 and window 27 in panel 14 provide a cooperating slot and tab lock for the fully folded retainer. The upper edge of panel 14 is reduced by S-cut 28 which, in cooperation with the indented upper curvature of end panel 24 and slot 23, define opening 29 in the folded package as illustrated in FIG. 5 to provide direct access to the central cavity of the folded package and through which the sutures are drawn during removal from the package.

Referring now to FIG. 2, there is illustrate the folder of FIG. 1 with winding pins 30 extending upward through openings 25. A bundle of needled sutures have been positioned with needles 31 retained between folded panels 11 and 12 and with suture strands 32 extending through slot 23 and wound around pins 30 in an upward extending figure-8 configuration. FIG. 2 further illustrates the extension of tab 22 beyond the edge of the package when panels 11 and 12 are folded to retain needles 31. Although FIG. 2 illustrates the suture bundle on pins 30 in the form of a circular wind, other winding configurations can be used, including a figure-8 and combinations of circular and figure-8 winds as described more fully in U.S. Pat. No. 4,089,409, incorporated herein by reference. After the suture has been fully wound on pins 30, panel 13 is raised against the winding pins, while panels 11 and 12 are angled upward to allow panel 14 to be inserted between suture strand 32 and panel 11 as illustrated in FIG. 3. Folding the package of FIG. 3 is completed by raising panels 11 and 12 whereupon panel 14 moves downward to enclose the suture and winding pins. Gussets 18 and 19 form side walls to space panels 13 and 14 and create an internal package cavity to accommodate the thickness of pins 30 and suture bundle 32. FIG. 3 further illustrates an optional feature of the packages of the present invention wherein panel 14 is scored along the outer edge to form end flap 36 which may be angled slightly toward the interior of the package as illustrated in FIGS. 2 and 3 to facilitate insertion of panel 14 under the suture bundle traversing panel 11 in order to bring this portion of the suture bundle into the interior cavity of the suture package. When the package is thus folded, the winding pins are withdrawn from the interior of the package, and the folded panels are locked by inserting tab 26 into window 27 as best illustrated in FIG. 4.

The fully folded package and suture of FIG. 3 is subsequently sterilized and sealed within sterile outer envelope 33 as illustrated in FIG. 4. Tab 22 projecting beyond the width of the folded retainer is secured in the seal area of envelope 33 as illustrated. Tear notch 34 is provided in the outer edge of envelope 33 and located approximately opposite the lower edge of tab 22 to facilitate opening of the suture package by tearing the outer envelope.

Envelope 33 is a conventional suture package envelope formed by heat sealing the periphery of two panels of aluminum foil coated on the interior surfaces thereof with a heat sealable polymeric composition 35 as illustrated in FIG. 4. Other means for sealing the envelope may be employed at the discretion of the practitioner.

Sutures packaged as illustrated in FIG. 4 are sterile and hermetically sealed and may be stored for extended periods of time. When the sutures are to be removed from the package, the outer envelope is opened by tearing from notch 34 as illustrated in FIG. 5. Since tab 22 is secured in the seal line of envelope 33 above notch 34, needle access panel 20 of panel 12 is simultaneously removed as the envelope is opened. As access panel 20 opens, envelope 33 is made to tear diagonally across the width of the suture package guided by the edge of die cut 21. Needles 31 are thereupon exposed and can be readily grasped with a needle holder in order to withdraw individual sutures from the central cavity of the suture package without removing the paper folder from the foil envelope as illlustrated in FIG. 5.

An optional feature of the illustrated package is upturn 37 of die cut 21 at foldline 16. This feature allows needle access panel 20 and the portion of envelope 33 secured thereto to be readily removed from the opened package by tearing along foldline 16. Removal of this portion of the opened package allows the inner suture retainer to be withdrawn from the foil envelope in its folded condition and with the needles and sutures contained therein.

The suture folder of the present invention is preferably constructed of a heavy weight, relatively stiff paper or paperboard such as 5 point to 12 point solid, bleached sulfate board. This paperboard is readily foldable and yet sufficiently strong and stiff to support the suture and provide a relatively rigid package. Similar materials including plastics, foils and laminates of these with each other or with paper can also be used with good results. The suture folder can be readily cut from such materials by a single die which also forms the desired foldlines including the necessary gussets in accordance with the present invention.

Sutures packaged in bundlles of 3 to 8 strands or more may be individually removed from the packages of the present invention by simply grasping an exposed end of a single suture and withdrawing the suture with a steady pull.

Sutures packaged in accordance with the present invention may be multifilament or monofilament sutures and multifilament sutures may be braided, twisted or covered. In addition, these sutures may be packaged with or without needles attached to the end of the suture which extends through the slot in panel 11 and is intended to be grasped in order to withdraw the suture from the package.

The preceding description has been directed primarily to a preferred embodiment of the present invention and many variations which nevertheless employ the essential features thereof will be apparent to those skilled in the art. For example, while the foregoing has described a folder to be employed with vertical winding pins, the suture may be coiled and positioned within the package by any convenient means which will permit single strand delivery from the folded package. Thus, the winding pin holes may be omitted in certain cases or other structures may be added as required by the intended folder loading method. These and other variations are accordingly included within the scope of the present invention.

What is claimed is:

1. An elongated, folded retainer for a plurality of surgical sutures comprising
    first and second needle retaining panels foldably connected along one major edge thereof, and
    third and fourth suture retaining panels foldably connected along one major edge thereof,
    said second needle retaining panel being further foldably connected to said third suture retaining panel along the other major edge thereof
    said second needle retaining panel having a tab extending beyond the foldline between the first and second needle retaining panels and a die cut extending diagonally toward the center and across the width of said panel from said tab to the foldline between said second and third panels to form a removable panel portion,
    said first needle retaining panel having a central opening and a slot extending from said opening to an outside edge of said panel, said central opening being positioned to underlie said removable panel portion of said second panel when said first and second panels are folded together, and
    said fourth panel having an upper edge contoured to avoid overlapping said central opening of said first panel when said retainer is in its folded configuration,
    said retainer when folded with said first and fourth panels enclosed between said second and third panels, forming an internal cavity between the third and fourth panels adapted to contain a plurality of surgical sutures coiled therein with one end of said sutures extending from said cavity through said central opening in the first panel to a point underlying said removable panel portion of said second panel.

2. A retainer of claim 1 including an end flap foldably connected to the end of the third panel adjacent the removable portion of the second panel and adapted to be folded over said third panel, the extremity of said flap being contoured to avoid overlapping the central opening in said first panel when said retainer is in a folded configuration.

3. A retainer of claim 2 wherein the extremity of said end flap in combination with the slotted opening in said first panel defines an aperture communicating between said second panel and the internal cavity of said retainer.

4. A retainer of claim 1 having integral locking means to secure said retainer in its folded configuration.

5. A retainer of claim 4 wherein said locking means comprises a tab bridging the foldline between said first and second panels and a corresponding cooperating slot in said fourth panel adjacent the foldline between said third and forth panels, whereby when said retainer is in its folded configuration, said tab engages said slot in a locking relationship.

6. A retainer of claim 1 including gussets formed by dual foldlines extending over a substantial portion of the length of the foldlines between said second, third and fourth panels.

7. A retainer of claim 6 including apertures for suture winding pins within the gusset between said second and third panels.

8. A retainer of claim 1 wherein the fourth panel includes a foldline defining a narrow flap along the other major edge thereof.

9. A retainer of claim 1 wherein said slot in said first panel forms a channel extending from the tab of said second panel to the opening in the first panel.

10. A suture package comprising in combination a folded retainer of claim 1 and a plurality of needled sutures, the needles of said sutures being positioned between said first and second panels with the sutures extending from between said panels through the opening in said first panel and into an internal cavity between said third and fourth panels, with the bulk of said suture being coiled between said third and fourth panels.

11. A suture package of claim 10 wherein said needles underlie the die cut in said second panel.

12. A suture package of claim 10 wherein said sutures are collated into a bundle of substantialy aligned strands and coiled between said third and fourth panels in a sequential figure-8 configuration.

13. A suture package of claim 10 enclosed in an outer envelope sealed around the periphery thereof.

14. A suture package of claim 13 wherein the tab of said second needle retaining panel extends into and is secured by the seal around the periphery of said outer envelope.

15. A suture package of claim 10 wherein said retainer is secured in its folded configuration by integral locking means.

16. A suture package of claim 10 wherein said needles are curved and are positioned with the outside of the curve oriented toward the foldline between said second and third panels.

* * * * *